US008263400B2

(12) United States Patent
Gambacurta et al.

(10) Patent No.: US 8,263,400 B2
(45) Date of Patent: Sep. 11, 2012

(54) METHOD FOR EXPANDING ADULT STEM CELLS FROM BLOOD AND COMPOSITIONS AND METHODS FOR USING THE SAME

(75) Inventors: Alessandra Gambacurta, Rome (IT); Marco Polettini, Sutri (IT)

(73) Assignee: Thankstem Srl, Udine (UD) (IT)

( * ) Notice: Subject to any disclaimer, the term of this patent is extended or adjusted under 35 U.S.C. 154(b) by 561 days.

(21) Appl. No.: 12/408,145

(22) Filed: Mar. 20, 2009

(65) Prior Publication Data

US 2010/0068189 A1 Mar. 18, 2010

Related U.S. Application Data

(63) Continuation-in-part of application No. PCT/EP2007/059531, filed on Sep. 11, 2007.

(30) Foreign Application Priority Data

Sep. 20, 2006 (IT) .............................. RM2006A0498

(51) Int. Cl.
*C12N 5/074* (2010.01)
*C12N 5/078* (2010.01)
*C12N 5/0789* (2010.01)
*C12N 5/02* (2006.01)

(52) U.S. Cl. ......... 435/325; 435/355; 435/372; 435/384

(58) Field of Classification Search ........................ None
See application file for complete search history.

(56) References Cited

FOREIGN PATENT DOCUMENTS

| WO | 03/083092 A | 10/2003 |
|----|-------------|---------|
| WO | 2004/043990 A | 5/2004 |

OTHER PUBLICATIONS

Office Action Issued Feb. 3, 2011 in EP Application No. 07820134.0.
Smith Austin: "A glossary for stem-cell biology", Nature, vol. 441, No. 7097, p. 1060 (2006).
Jorg Fiedler, et al.; "IGF-I and IGF-II stimulate directed cell migration of bone-marrow-derived human mesenchymal progenitor cells"; Biochemical and Biophysical Research Communications, vol. 345; pp. 1177-1183 (2006).
Linda G. Griffith, et al.; "Tissue Engineering—Current Challenges and Expanding Opportunities"; Science; vol. 295; pp. 1009-1014 (Feb. 8, 2002).
Rajiv Gulati, et al.; "Diverse Origin and Function of Cells With Endothelial Phenotype Obtained From Adult Human Blood"; Circ. Res. 2003; vol. 93; pp. 1023-1025 (2003).

Mai Hou, et al.; "Transplantation of mesenchymal stem cells from human bone marrow improves damaged heart function in rats"; International Journal of Cardiology; vol. 115; pp. 220-228 (2007).
Won Jun Kang, et al.; "Tissue Distribution of 18F-FDG-Labeled Peripheral Hematopoietic Stem Cells After Intracoronary Administration in Patients with Myocardial Infarction"; The Journal of Nuclear Medicine; vol. 47; No. 8; pp. 1295-1301 (Aug. 2006).
Martin Korbling, et al.; "Hepatocytes and Epithelial Cells of Donor Origin in Recipients of Peripheral-Blood Stem Cells"; New England Journal of Medicine; vol. 346; No. 10; pp. 738-746 (Mar. 7, 2002).
Masataka Kuwana, et al.; "Human circulating CD14+ monocytes as a source of progenitors that exhibit mesenchymal cell differentiation"; Journal of Leukocytes Biology; vol. 74; pp. 833-845 (Nov. 2003).
Tatsuma Okazaki, et al.; "Macrophage Colony-Stimulating Factor Induced Vascular Endothelial Growth Factor Production in Skeletal Muscle and Promotes Tumor Angiogenesis"; The Journal of Immunology; vol. 174; pp. 7531-7538 (2005).
M. Rabinovitch, et al.; "Cell Shape Changes Induced by Cationic Anesthetics"; The Journal of Experimental Medicine; vol. 143; pp. 290-304 (1976).
Troy D. Randall, et al.; "Characterization of a Population of Cells in the Bone Marrow that Phenotypically Mimics Hematopoietic Stem Cells: Resting Stem Cells or Mystery Population?"; Stem Cells; vol. 16; pp. 38-48 (1998).
AJ Wagners, et al.; "Cell fate determination from stem cells"; Gene Therapy; vol. 9; pp. 606-612 (2002).
YS Zhang, et al.; "Preliminary research on preparation of porcine bladder acellular matrix graft for tissue engineering applications"; Zhonghua Yi Xue Za Zhi; vol. 85; No. 38; pp. 2724-2727 (Oct. 12, 2005) (English Abstract Only).
Yong Zhao, et al.; "A human peripheral blood monocytes-derived subset acts as pluripotent stem cells"; PNAS; vol. 100; No. 5; pp. 2426-2431 (Mar. 4, 2003).
Maud Condomines. et al.; "Functional Regulatory T Cells Are Collected in Stem Cell Autografts by Mobilization with High-Dose Cyclophosphamide and Granulocyte Colony-Stimulating Factor"; The Journal of Immunology; vol. 176; pp. 6631-6639 (2006).
R. K. W. Smith, et al.; "Isolation and implantation of autologous equine mesenchymal stem cells from bone marrow into the superficial digital flexor tendon as a potential novel treatment"; Equine Veterinary Journal; vol. 35; No. 1; pp. 99-102 (2003).

*Primary Examiner* — Daniel C Gamett
(74) *Attorney, Agent, or Firm* — Panitch Schwarze Belisario & Nadel LLP

(57) ABSTRACT

A method for the expansion of adult stem cells from blood, particularly but not only peripheral blood, involves removing adult stem cells from blood of a mammal, immediately expanding the stem cells via in-vitro treatment with MCSF (Macrophage Colony Stimulating Factor) at a concentration of about 8-15 nM, and purifying the expanded stem cells. Compositions and methods of using the expanded adult stem cells are also described.

12 Claims, 13 Drawing Sheets

METHOD FOR EXPANDING ADULT STEM CELLS FROM BLOOD AND COMPOSITIONS AND METHODS FOR USING THE SAME

CROSS-REFERENCE TO RELATED APPLICATIONS

This application is a Continuation-in-Part of International Application No. PCT/EP2007/059531, filed Sep. 11, 2007, which was published in the English language on Mar. 27, 2008 under International Publication No. WO 2008/034740, and the disclosure of which is incorporated herein by reference.

BACKGROUND OF THE INVENTION

The present invention concerns a method for expanding stem cells from blood, particularly but not only peripheral blood, of adult mammals, and the relative application in the medical field, in particular in the veterinary field, for the treatment of lesions, chronic and/or acute inflammatory pathologies, and neurological and neurodegenerative pathologies. Here, and hereafter in the description, and as is known in literature, the terms "expanding" and "expansion" refer to the process of increasing the number of cells either by cell division or, as in the specific case described and claimed, by "de-differentiation", that is, the process by which the cells present in the blood are transformed into stem cells following suitable in-vitro treatment, as will be seen hereafter.

In recent years the use of stem cells in therapy has had great approval due to the successes obtained in treating various pathologies which were previously thought incurable. However, processes known until now for obtaining stem cells have been laborious and expensive.

Pluripotent stem cells (PSC) are a source available not only for research but also for the creation of drugs and for transplants (A. J. Wagers et al., "Cell fate determination from stem cells"; *Gene Therapy;* 9; 606-612 (2002); L. G. Griffith et al., "Tissue Engineering—Current Challenges and Expanding Opportunities"; *Science;* 295; 1009 (2002)).

There are two ample categories of stem cells: embryonic and adult. The former are derived from embryos, and more exactly from 8-day blastocysts, whereas adult stem cells may be obtained mainly from bone marrow, adipose or muscular tissue, or from peripheral blood.

The definition of stem cell is constantly evolving and, at the moment, there is no general consensus or standard method to isolate or identify them. For all these cells, embryonic (ES) and adult, both hematopoietic (HSC) and mesenchymal (MSC) (M. Kuwana et al., "Human circulating CD14$^+$ monocytes as a source of progenitors that exhibit mesenchymal cell differentiation"; *J. Leuk Biol;* 74; 833-845 (2003)), different genetic markers have been identified, of which some are common to many cell types. (See, for example M. Condomines et al., "Functional Regulatory T Cells Are Collected in Stem Cell Autographs by Mobilization with High-Dose Cyclophosphamide and Granulocyte Colony-Stimulating Factor"; *J. Immunology;* 176: 6631-6639 (2006); W. J. Kang et al., "Tissue Distribution of $^{18}$F-FDG-Labeled Peripheral Hematopoietic Stem Cells After Intracoronary Administration in Patients with Myocardial Infarction"; *J. Nucl Med.;* 47:1295-1301 (2006); Y. Zhao et al., "A human peripheral blood monocyte-derived subset acts as pluripotent stem cells"; *PNAS;* vol. 100, No. 5; 2426-2431 (2003); and M. Rabinovitch et al., "Cell Shape Changes Induced by Cationic Anesthetics"; *J. Experimental Medicine;* 143; 290-304 (1976)).

In particular, Zhao Y. et al. ("A human peripheral blood monocyte-derived subset acts as pluripotent stem cells"; *PNAS;* vol. 100, No. 5; 2426-2431 (2003) and WO 2004/043990) discloses a method for preparing monocyte-derived stem cells which includes the steps of isolating a peripheral-blood monocyte, contacting it with a mitogenic component, and subsequently culturing the peripheral-blood monocyte under conditions suitable for the propagation of the cells.

This method, which requires a first step of isolating the monocyte and a subsequent expansion step in a culturing media, requires very long times, on the order of 15-20 days, to obtain a significant number of stem cells. By this method, it is not possible to obtain stem cells of the totipotent type, that is, cells that are non-specialized and suitable to be directly inoculated into the patient after a very short time from the first drawing.

Numerous scientific works describe stem cells' ability to regenerate different types of lesions by regenerating tissues that are mechanically damaged or are damaged by various pathologies, thus eliminating at the root the causes that generated the pathology and not simply acting on the effects thereof.

At the moment, research is more oriented toward the use of stem cells isolated from embryonic tissue, fetuses, or the umbilical cord, but this work is raising various legal and ethical questions. Above all, as of today the use of these cells brings various contraindications, such as risk of infection, risk of rejection if transplanted and, in horses, the risk of onset of teratomas.

To obviate these problems, it has therefore been contemplated to use in the "in vivo" therapy autologous stem cells isolated preferably from bone marrow, adipose tissue or peripheral blood. These methods, starting from adult stem cells, provide a step of differentiation "in-vitro" (or "ex vivo") of the stem cells in the cell line desired by means of specific differentiation induction factors, and a subsequent step of "in vivo" transplantation of the differentiated cell line obtained. In these methods, the limit is due to the fact that observable rejection phenomena occur because the differentiated cells re-introduced into the patient are not recognized as self-cells, but lose the self-recognition factors during the differentiation step induced in-vitro.

In humans, taking stem cells from peripheral blood entails purifying them through a process called "aphaeresis" or "leucophaeresis". In practice, the cells are extracted from the blood, collected, and then inoculated into patients immediately after chemo- or radio therapy. In aphaeresis, which lasts from 6 to 8 hours, the blood is taken from the vein of an arm or a vein in the neck or the chest, and made to pass through a machine which removes the stem cells. The blood, thus purified, returns to the patient, while the cells collected are preserved by means of refrigeration in liquid nitrogen (M. Condomines et al., "Functional Regulatory T Cells Are Collected in Stem Cell Autographs by Mobilization with High-Dose Cyclophosphamide and Granulocyte Colony-Stimulating Factor"; *J. Immunology;* 176: 6631-6639 (2006); W. J. Kang et al., "Tissue Distribution of $^{18}$F-FDG-Labeled Peripheral Hematopoietic Stem Cells After Intracoronary Administration in Patients with Myocardial Infarction"; *J. Nucl Med.;* 47:1295-1301 (2006)). This technique is not only painful, but also extremely stressful for the patient. Furthermore, it is impracticable for animals of either small or large size; above all, the technique does not provide a real discrimination and/or purification of the stem cells circulating.

At present, in veterinary science, stem cells are used successfully mainly in the reconstruction of tendons and ligaments with lesions. The main techniques for purification include:

use of growth factors or platelet derivatives (TGF-B, VEGF), but the economic costs of extracting these are prohibitive (M. Hou et al., "Transplantation of mesenchymal stem cells from human bone marrow improves damaged heart function in rats"; *International Journal of Cardiology;* 115; 220-228 (2006));

isolation of stem cells taken from bone marrow. This technique provides for purification and then use for therapy of only 15% of the cells contained in the material extracted;

isolation of stem cells taken from adipose tissue. This technique, which requires the prior surgical removal of considerable quantities of tissue from the donor animal, does not allow for intravenous administration;

IGF-1 (insulin-like growth factor 1), known as Tendotrophin (J. Fiedler et al., "IGF-I and IGF-II stimulate directed cell migration of bone-marrow-derived human mesenchymal progenitor cells"; *Biochemical and Biophysical Research Communications;* 345; 1177-1183 (2006));

UBM (urinary bladder matrix), a derivative from the pig containing cytokines (but not nucleate cells), which induces the cicatrization of the wound but not the regeneration of the zone with lesions (Y. S. Zhang et al., "Preliminary research on preparation of porcine bladder acellular matrix graft for tissue engineering applications"; *Zhonghua Yi Xue Za Zhi;* 85(38); 2724-2727 (2005)).

In the light of all the above, it is obvious that methods are needed for the expansion and purification of adult stem cells from easily accessible sources which must also provide for obtaining stem cells suitable for use as medication in the medical-veterinary field. Once administered in the mammal, such cells do not give rise to phenomena of rejection and are easy to preserve.

There is also an obvious need for obtaining stem cells of the pluripotent and totipotent type, that is, non-specialized cells, which can be inoculated directly into the patient with much shorter production times than those provided at present.

BRIEF SUMMARY OF THE INVENTION

The authors of the present invention have now perfected a method for the expansion and purification in-vitro of stem cells from peripheral blood. The method provides for obtaining stem cells which do not give collateral effects, such as phenomena of rejection, infection, or teratomas. Preferably, once administered in the adult mammal, these cells are able to be differentiated "in vivo" and to behave as pluripotent stem cells.

Applicants have seen that the cells thus expanded, once injected locally or intravenously, acquire "in vivo" (and not "in-vitro", as in known methods in the state of the art by means of suitable growth factors and/or chemical stimuli (R. Gulati et al., "Diverse Origin and Function of Cells with Endothelial Phenotype Obtained from Adult Human Blood"; *Circ. Res.;* 93; 1023-1025 (2003); M. Korbling et al., "Hepatocytes and Epithelial Cells of Donor Origin in Recipients or Peripheral-Blood Stem Cells"; *New England Journal of Medicine;* 346: 738-746 (2002); and T. Okazaki et al., "Macrophage Colony-Stimulating Factor Induces Vascular Endothelial Growth Factor Production in Skeletal Muscle and Promotes Tumor Angiogenesis"; *J. Immunology;* 174: 7531-7538 (2005)) all the morphological and chemical characteristics of macrophagic, lymphocytic, epithelial, endothelial, neuronal and hepatocyte cells, according to the needs and pathologies of the animals treated. The method is even less invasive than other methods used until now to collect stem cells, painless (if compared with aphaeresis), economical, and technically the most suitable to be used in all animal species (small and large).

Finally, the possibility of obtaining these cells easily, and then being able to preserve them for a long time refrigerated in liquid nitrogen, makes the cells obtained by the method according to the invention suitable for autologous transplants, for the treatment of many human and veterinary pathologies (including lesions of various types, metabolic illnesses, acute and chronic neurological and inflammatory pathologies) and for the improvement of competitive performances of some animals, such as horses.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

The present invention therefore specifically concerns a method for expanding adult stem cells from blood, particularly but not limited to peripheral blood, comprising the following steps.

The first step in the method of the invention involves removing adult stem cells from the blood (preferably, but not limited to peripheral blood) of an adult mammal. Subsequently, the method involves expanding the stem cells of blood immediately after they have been removed from the adult mammal via an in-vitro treatment with MCSF (Macrophage Colony Stimulating Factor) at a concentration of about 8-15 nM, preferably about 10 nM. The duration of the expansion step may vary according to the conditions in which the in-vitro treatment is carried out. Applicants have determined experimentally that a duration of in-vitro treatment with MCSF of about 24 to 96 hours, advantageously about 48 to 72 hours, leads to a stabilization of the expansion with identification of the simultaneous presence of the markers CD 90, CD34 and mixed CD 90/CD 34. Accordingly, this duration is considered optimum, but other durations would also be within the scope of the invention.

The term "immediately" is intended to mean the shortest possible time between the blood cells being removed from the mammal and the beginning of the in-vitro treatment. In any case, the time should preferably be not more than about 10 minutes and advantageously not more than about 5 minutes to avoid blood coagulation and to obtain the desired number of stem cells number in the shortest amount of time between the removal of the blood sample and the final treatment.

Following the expansion, a further step in the method of the invention involves purification of the expanded stem cells, preferably by means of fractioning on a Ficoll gradient. This purification step is fundamentally intended to destroy the red corpuscles.

Therefore, contrary to the state of the art, the presently claimed invention provides a step of expansion of the stem cells by contacting them with MCSF and a possible anticoagulant product, for example in a suitable test tube. This expansion step is performed immediately after the stem cells of blood have been removed from the patient, without isolating specific parts of them and without using any culturing media. A preferred embodiment of the present invention concerns the expansion method for stem cells from peripheral blood of adult mammals.

In a preferred embodiment, following the purification step, the purified cells are further expanded via in-vitro treatment with MCSF at a concentration of about 35-55 nM, preferably about 50 nM, more preferably about 45 nM. This duration of this step may also vary from about 24 to about 96 hours, preferably about 48 to 72 hours. In one preferred embodiment, at least one of the expanding steps is performed for about 25 to 48 hours, preferably about 45 to 48 hours.

Figure 12:
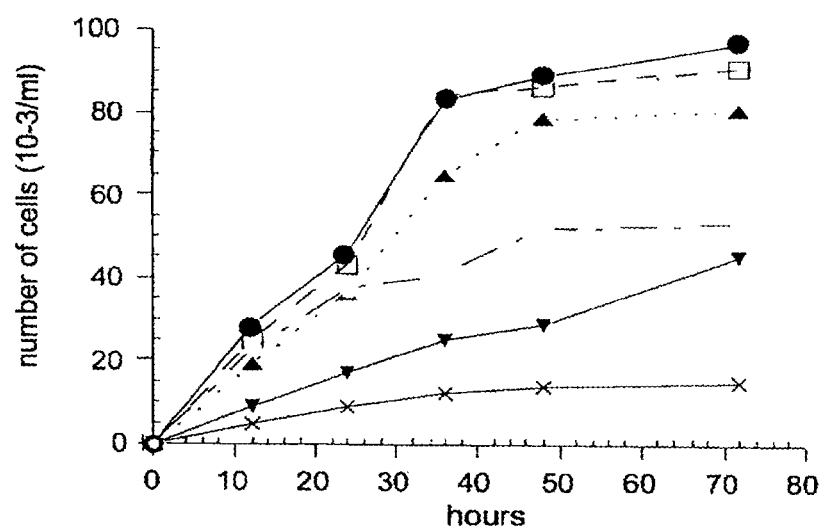
FIG. 12 is a graph of the number of cells obtained using different quantities of MCSF in one embodiment of the present invention.

It has been observed that when MCSF is used at a concentration greater than about 55 nM (i.e., about 70 nM), after 24 hours the cells already did not maintain the phenotype of pluripotent stem cells (see FIG. 12). Specifically, the graph in FIG. 12 depicts the number of cells obtained using different concentrations of MCSF: 15 nM (broken line with crosses), 25 nM (broken line with triangles, apex down), 35 nM (broken line with triangles, apex up), 50 nM (broken line with black circles), 60 nM (broken line with white squares), and 70 nM (broken line with white circles). In each case, the results represent the average number of cells counted from three samples of peripheral blood.

Figure 13:
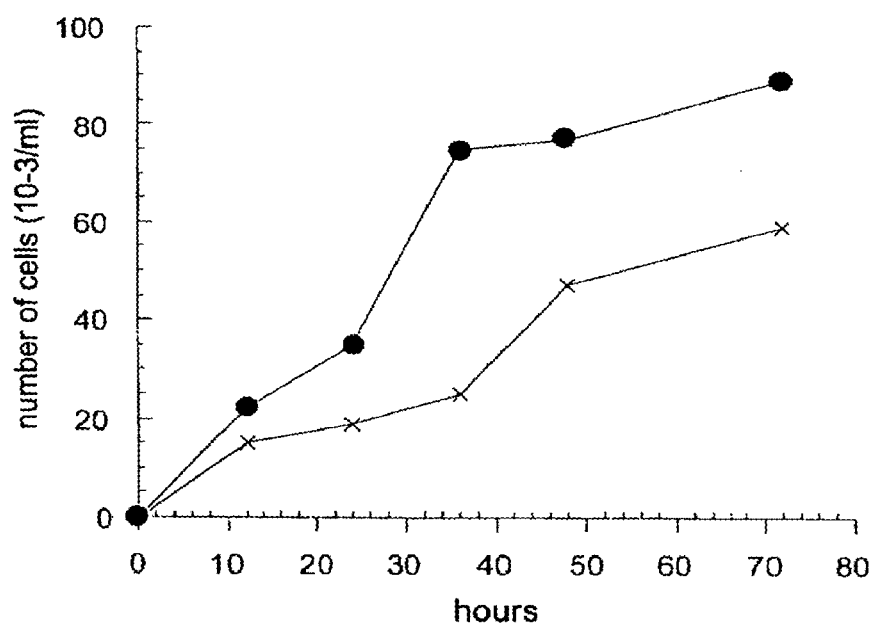
FIG. 13 is a graph of the number of cells obtained from peripheral blood v. time for cells pretreated with and not treated with MCSF.

In particular, the first step of prior expansion in suspension with MCSF immediately after the blood has been removed provides for an increase in the percentage of stem cells (see FIG. 13). Specifically, the graph in FIG. 13 depicts the number of cells obtained from peripheral blood after the first expansion step according to the method of the invention. The broken line with dots represents cells that were pre-treated with MCSF whereas the broken line with crosses represents cells that were not treated with MCSF. In each case, the results represent the average of cells counted from three samples of peripheral blood. The subsequent expansion step in one embodiment of the invention provides for obtaining pluripotent stem cells which are differentiated directly in vivo, without causing phenomena of rejection or infection.

The invention also relates to a method of utilizing the expanded adult stem cells obtained according to the expansion method described above for the preparation of a medication for treating lesions of mammals. The treatable lesions include, without limitation, cutaneous lesions, lesions to tendons, lesions to ligaments, bone lesions, lesions to the mucous membranes, and fractures.

The present invention also relates to a method of utilizing the expanded adult stem cells obtained according to the method described above for the preparation of a medication for treating neurological or neurodegenerative pathologies in mammals, including, without limitation, Cushing's disease, head shaking, Wobbler's syndrome, breathing difficulties, paresis of the limbs; acute or chronic inflammatory pathologies such as laminitis, periostitis, gastritis, arthrosis, inflammations caused by viral, bacterial, parasite, and/or mycotic agents; and dilatation-torsion of the stomach.

A method is also provided for utilizing the expanded adult stem cells obtained by the method according to the invention for treating infertility in mares, precocity in colts and for improving competitive performance or activity in mammals.

The present invention also relates to a pharmaceutical composition comprising an active principle comprising the expanded adult stem cells obtained according to the expansion method described above and at least one pharmacologically acceptable adjuvant and/or excipient. Such adjuvants and excipients are well known to those skilled in the art and need not be described.

In a first particularly preferred composition, formulated for intravenous injection, the adult stem cells are contained at a concentration of about $90\text{-}250 \times 10^3$ cells/ml in the composition, preferably about $150 \times 10^3$ cells/ml. A second preferred composition according to the invention may be formulated for local application, as well as for topical application in the case of external wounds. Such a composition preferably comprises the adult stem cells obtained according to the expansion method defined above at a concentration of about $4\text{-}40 \times 10^6$ cells/ml in the composition.

The pharmaceutical compositions mentioned above may also comprise an antibiotic as an active principle at a concentration of about 5-15 nM, preferably 10 nM. Preferably, the antibiotic is gentamicin or amicacin.

The invention also relates to a method of using the second pharmaceutical composition as described above (i.e., suitable for local application, with or without antibiotic) as a medication for treating lesions in mammals, such as, but not limited to cutaneous lesions, lesions to tendons, lesions to ligaments, bone lesions, and lesions to mucous membranes.

According to another feature, the invention also relates to a method of using this pharmaceutical composition (i.e., suitable for local application, with or without antibiotic) as a medication for treating fractures in mammals.

The present invention also includes a method of using the first pharmaceutical composition described above (i.e., suitable for intravenous administration), as a medication for treating neurological or neurodegenerative pathologies in mammals including, without limitation, Cushing's disease, head shaking, Wobbler's syndrome, breathing difficulties, and paresis of the limbs.

A further method of the invention relates to using this pharmaceutical composition (i.e. suitable for intravenous administration), as a medication for treating acute or chronic inflammatory pathologies in mammals such as, but not limited to laminitis, periostitis, gastritis, arthrosis, and inflammations caused by viral, bacterial, parasite, and/or mycotic agents.

Finally, the invention also relates to a method of using the first pharmaceutical composition described above (i.e., suitable for intravenous administration), as a medication for treating the syndrome of dilatation-torsion of the stomach in mammals. This pharmacological composition according to the invention may also be used for treating pathologies of the gall bladder, cardiovascular pathologies, stress with consequent depression and, in breeding, infertility of mares and precocity of colts, and also for improving the competitive activities or performances of mammals.

In each of the above methods, the expanded adult stem cells are preferably contained in the pharmaceutical composition at a concentration of about $150 \times 10^3$ cells/ml and the medication is administered once a week intravaneously.

Preferably, the methods described above have particular application to the veterinary field. The mammals treated may be horses, dogs, cats, or humans, for example.

The cells isolated from peripheral blood act "in vivo" as pluripotent stem cells (PSC) following the expansion according to the invention and are able to resolve, within the space of a few months, lesions or pathologies incurable or curable only slowly with classical methodologies and/or drugs. The effects of the inventive method may be seen in conjunction with the following, non-limiting, examples.

Materials and Methods

Sampling

Each sample of peripheral blood consisted of about 5-7 ml, was taken from the lower limbs of horses and dogs, and was immediately put into test tubes containing, for example, heparin (150 U), and MCSF (10 nM). However, the heparin could be replaced by another suitable anti-coagulant substance.

Purification

The blood samples (5-7 ml) were diluted 1:5 in PBS (Phosphate Buffer Saline) containing $NH_4Cl$ (200 mM) to cause the lyses of the red corpuscles, centrifuged at 10,000 g, washed twice with PBS, and centrifuged again at 200 g. The nucleate cells obtained were incubated for 7-12 hours at 37° C., preferentially for 10-12 hours, and purified by means of fractioning on a Ficoll gradient, then isolated and washed three times with RPMI medium 1640 (Life Technologies, Grand Island, N.Y.). Once purified, the cells that contained about 95% cells with CD90 phenotype (as determined by means of cytofluorometric analysis by means of a FACScan—Becton Dickinson flow photometer), were incubated for another 24 hours in 50 ng/ml MCSF 45 nM, expanded to obtain the number of cells necessary for the local or centrifuged treatments at 10,000 g and re-suspended in PBS at a concentration of about $90 \times 10^3$ cells/ml for intravenous treatments.

Immunostaining

For cytophenotyping, the cells were washed in PBS and then fixed on slides in 4% formaldehyde in PBS for 20 mins at 20° C.

To identify the intra-cellular proteins, the cells were permeabilized with 0.5% Triton X-100 for 5 mins at 20° C. and then incubated for 1 hour with the primary antibodies diluted in PBS containing 1% BSA (to block the aspecific antigenic sites). After three successive washes, the slides were incubated for 45 mins with the secondary antibody conjugate with the most appropriate fluorochrome: FITC or tetramethylrhodamine B isothiocyanate (TRITC) or Cy5.

All of the secondary antibodies were developed, using the donkey as host, by Jackson ImmunoResearch. The immunocytochemistries were carried out at temperature of 4° C. and in a humidity saturated atmosphere. After three washes, the slides were mounted using "gelvatol-PBS". The fluorescence images were then acquired by means of a fluorescence microscope using as an internal standard an immunofluorescence directed against the glyceraldehyde 3-phosphate dehydrogenase (polyclonal sheep antibody produced by Cortex Biochem, San Leandro, Calif.). As negative controls and in order to calibrate the levels of the fluorescence background, slides incubated with aspecific antibodies of the same isotype as the samples involved were used.

The images that were obtained show the cells seen through a phase contrast microscope, superimposed on the fluorescence image of the lipids colored with Nile Red and on the image of the nuclei colored with DAPI (4',6-diamidin-2-phenylindole). The reference bar measures 40 µm. The intensity of relative fluorescence was examined by means of quantitative ratio imaging microscopy between cells treated with MCSF and macrophages.

The method described above was used to identify all the markers investigated (CD 90, CD 34, and CD90/CD34).

Results

Local Use

The cells were applied directly in the cases of external wounds. On the contrary, in the case of lesions to tendons, ligaments, and fractures, the cells were inoculated directly into the site of the lesion at a final concentration, except where otherwise indicated, of $5-10 \times 10^6$ cells/ml according to the seriousness of the lesion. In cases where the cells could not be inserted precisely in the lesions the following methodology was followed. For lesions to collateral ligaments, the injection was made between the second and third phalange. For lesions to the naviculars, the injection was made in the carpal tunnel. Finally, for lesions to the sacroiliac articulations and in cases of Wobbler, the injection was made between the fifth and the sixth cervical or between the sixth and the seventh cervical.

Cutaneous Lesions

Figure 1:
FIG. 1 is photograph of a lesion of 20 cm diameter between the metatarsus and the first phalange with clostridia and destruction of the extensor tendon in a mare.
Figure 2:
FIG. 2 is a photograph of the same mare of FIG. 1 three months after the local application to the lesion of the stem cells according to the invention.
Figure 3:
FIG. 3 is a photograph of the mare after six months of treatment of the lesion.
Figure 4:
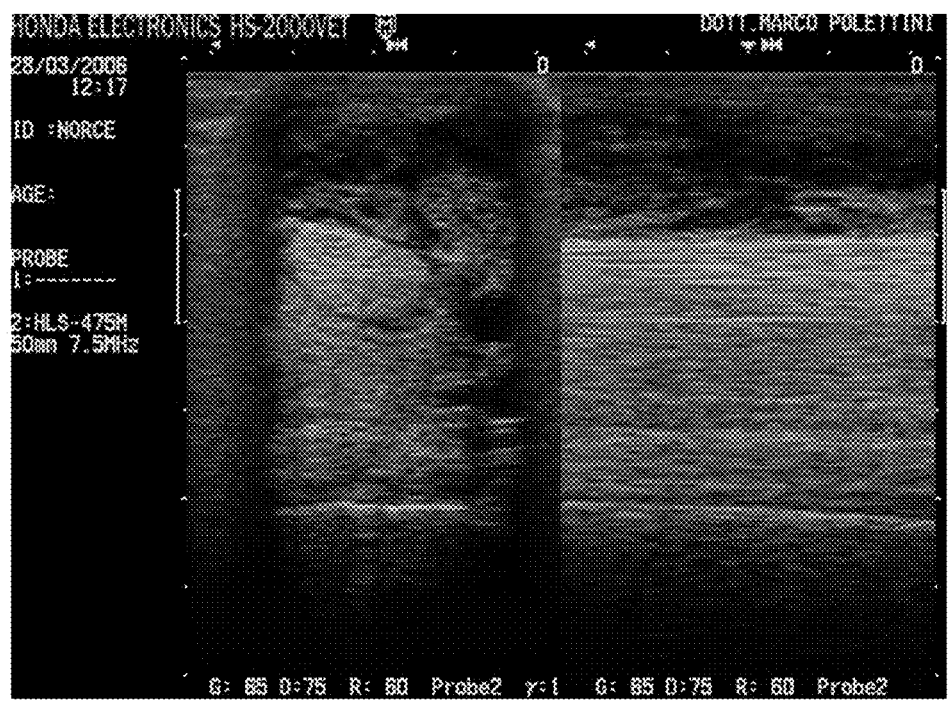
FIG. 4 is a ultrasound scan of a horse with a lesion of 80% of the surface flexor tendon.
Figure 5:
FIG. 5 is a ultrasound scan of the horse about three and a half months after the local treatment with stem cells according to the invention.
Figure 6:
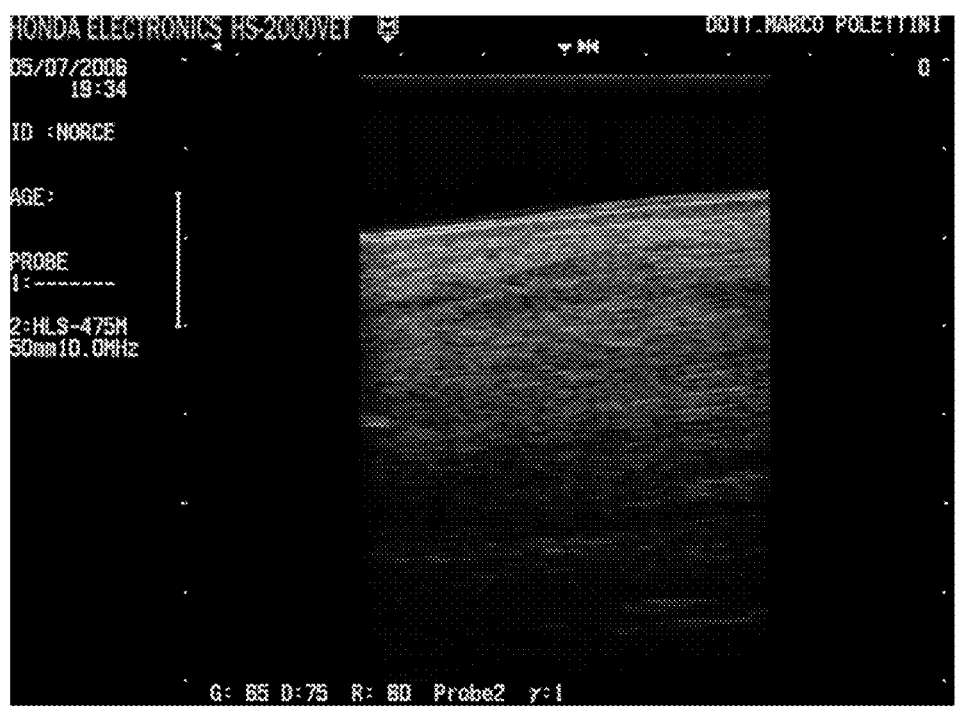
FIG. 6 is a further ultrasound scan of the horse about three and a half months after the local treatment with stem cells.
Figure 7:
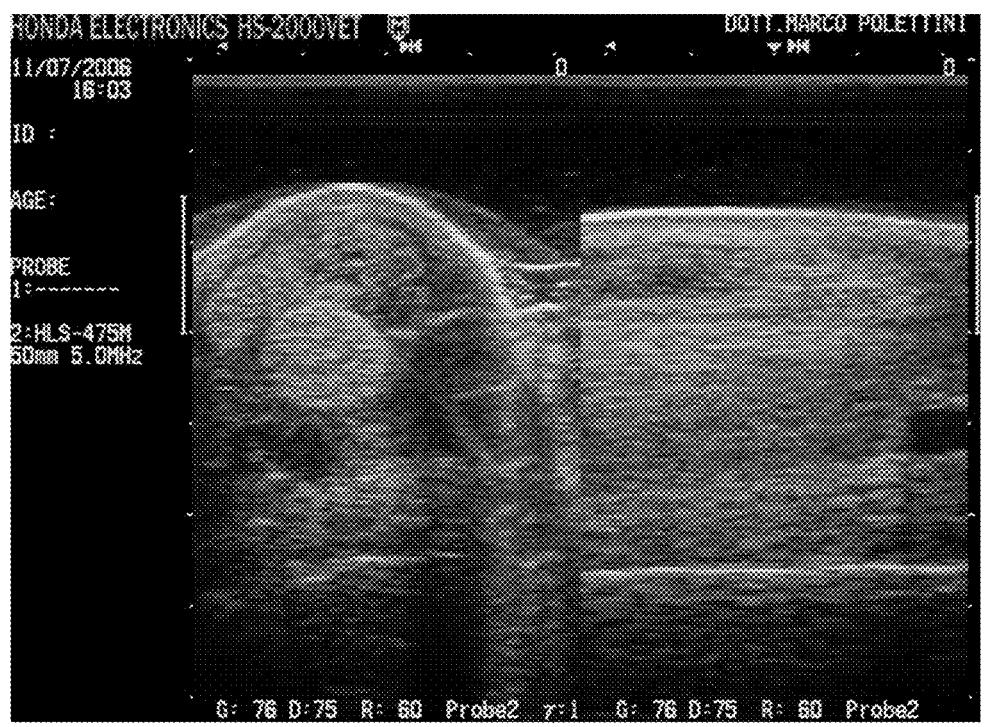
FIG. 7 is a ultrasound scan of the horse after about four months of the local treatment, depicting nearly complete regeneration of the tendon and the lack of scar tissue.

This involved the case of a mare with a wound between the metatarsus and first phalange, 20 cm in diameter with clostridia complications which had led to the destruction of the underlying tissues, including the extensor tendon (FIG. 1). The first application was made one year after the accident and after two surgical operations to remove the cheloids, and was repeated three more times at intervals of 15 days, using from 10 to $400 \times 10^6$ cells re-suspended in a physiological solution in the presence of gentamicin. After 100 days, the wound was completely healed (FIG. 2), and after 6 months the hair had re-appeared in 70% of the scar zone (FIG. 3).

Tendons

Three horses were treated with lesions of 80% of the superficial flexor tendon. After three months of treatment with about $300 \times 10^6$ cells, hypoecogenic zones were no longer seen upon ultrasound exam. In fact, it was observed that the thickness of the tendon (which had increased after the laceration and the inflammatory processes) was visibly reduced by 80%, as can be seen from the ultrasound scans shown in FIGS. 4-7.

Figure 8:
FIG. 8 is a ultrasound scan of a mare with a smaller tendon lesion of less than 1 cm in diameter.
Figure 9:
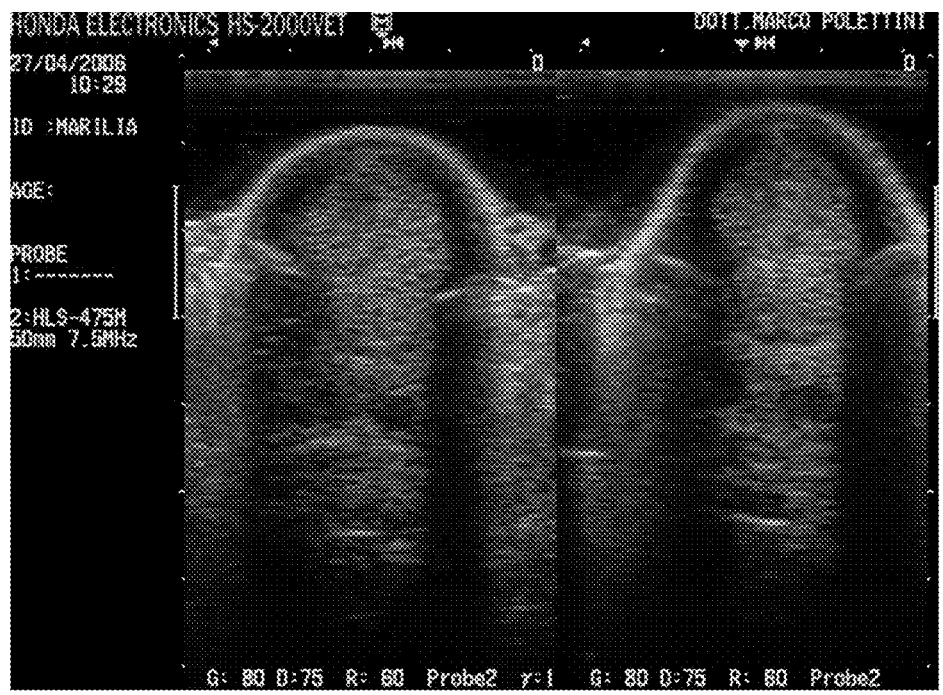
FIG. 9 is a ultrasound scan of the same mare in after a month of the local treatment by a method of the invention.

Other horses with smaller lesions to the tendon (1 cm in diameter) no longer showed the lesion one month after treatment (FIGS. 8 and 9).

Ligaments

Among the lesions treated included an insertion of the suspender ligament under the hock with consequent lameness. Less than three months after a local inoculation, the horse starting working again, without lameness, and after one year there was no relapse.

Other horses treated, which had lesions between the branches and the central body of the suspender ligament, front and rear, were all resolved with restitutio ad integrum.

Fractures

Among the fractures treated included the case of a dog with a fractured femur which, after 4 months following a surgical operation, was still not forming bone callus. After a local application of $10 \times 10^6$ cells, there was a complete recovery in 30 days.

Mucous Membranes

With regard to the healing of lesions to the mucous membranes, various chronic ulcers were treated. The most sensational case was that of a dressage horse with several ulcers in the mouth which had already had two plastic surgery operations. Following the treatment, the horse stopped bleeding within three days after local application of $4 \times 10^5$ cells. After 15 days, the lesions were completely healed.

These results clearly demonstrate that the local application of isolated cells enriched by the inventive method on tendons, ligaments, joints and fractures provided complete resolution for more than 80% of the cases examined within a few weeks or, at most, within four months. The remaining 20% of cases showed considerable improvements. The methods commonly used today in veterinary science in these cases give positive results in not more than 60% of cases after a treatment of about 6-15 months, and improvements in only 5% of cases. Accordingly, the results achieved by the inventive methods are a dramatic improvement over prior art methods.

Intravenous Use

Cells were used intravenously (1 dose=$150 \times 10^3$ cells) in the following pathologies:

Gushing's disease is a pathology due to hypertrophy of the intermediate hypophysis with reduced production of dopamine by the hypothalamus. This condition is very similar to Parkinson's disease in humans.

An affected pony was treated, which also had, apart from the classic symptoms of the disease, reduced immune defenses with hemolysis. After three treatments at an interval of 5 days with $150 \times 10^3$ cells per treatment, improvements were noticed. After 4 cycles repeated at intervals of 40 days, the symptoms completely disappeared. The treatment of another four horses in the same way produced the same results.

Head shaking is a neurological pathology of the central nervous system with secondary complications of the trigeminus, which leads to continuous head shaking and problems of photophobia. The horse treated had these symptoms for six months. The treatment entailed a cycle of $150 \times 10^3$ cells at intervals of one week for 5 weeks. Already in the third week, the symptoms had disappeared. Two other horses treated with the same protocol showed the same results.

Three cases of Wobbler. This is a congenital cervical neurological compression. The cases treated by administering three doses (intravenously and local) at an interval of a week showed complete remission of the symptoms following treatment.

The intravenous use of expanded and purified stem cells using the method described showed how these cells are able "in vivo" to resolve pathologies affecting the neuronal tissue and to give results after a week of treatment.

Vascular reconstruction. In a horse affected by laminitis (destruction of the peripheral vascularization in the foot, with the result of an extremely painful lameness such as to prevent movement), the pain had almost disappeared 12-24 hours after a dose was administered, inoculated into the digital vessels. The same result was obtained for two other cases of horses affected by the same pathology.

Figure 10:
FIG. 10 is a photograph of a 17-year-old horse with general weakness, operated for colic, before treatment with the stem cells according to the invention.
Figure 11:
FIG. 11 is a photograph of a performance of the 17-year-old horse one year after intravenous treatment with the stem cells according to the invention.

Other general cases in which the cells were administered intravenously were:

A case of a horse with a fracture of the navicular which restarted its competitive activity after the simultaneous administration of the stem cells in the peripheral vessels, the navicular bursa and the articular surface between the deep flexor tendon and the navicular bone;

A case of a horse suffering from periostitis which, with the administration of two intravenous doses, improved its lameness;

A case of a seventeen year old horse operated for colic and afterward put to grass because it was no longer able to continue competitive activity due to a persistent state of general debilitation. After four cycles of three doses every five days, the horse started competitive activity again, participated in competitions and obtained results it had never had before achieved (FIGS. 10 and 11);

A case of a twenty-year-old horse with suspected cerebral ischemia with consequent loss of coordination in three limbs which, after pharmacological treatment based on cortisone derivatives, still continued to keep an uncertain and staggering pace. After the administration of two doses at an interval of one week, the animal restarted its normal activity without showing any symptoms;

A case of a twenty-three year old mare, with a pregnancy at 21 years of age, which, after the period of lactation had finished, was treated with two doses of cells intravenously. After the treatment the mare restarted her competitive activity in full. (At 20, a horse is considered too old for competitive activity);

A case of a horse with a fractured pelvis which, after two doses of cells, restarted international competitive activity;

A case of a fifteen-year-old horse with breathing difficulties and a very nervy character, which, after treatment with two doses, started competing again on an international level without the slightest breathing difficulty;

A case of two horses with extreme lameness for more than two years consequent to the pulling of the collateral ligament between the first and second phalange. This pathology is considered irreversible in 75% of cases. After treatment with three doses for three months, both animals treated returned to competing normally;

A case of a thirteen-year-old horse operated for colic at seven and castrated at age twelve. Following the second operation, the animal had non-emittent bacterial complications despite treatment with antibiotics and anti-inflammatories. Moreover, the animal suffered from chronic gastritis, proved by a gastroscopy. After the administration of four doses at an interval of one week, the horse was again given a gastroscopy which showed the complete regeneration of the gastric mucous membrane. The same result was obtained on ten other gallop horses;

A case of a horse with a pansystolic murmur and numerous murmurs atypical to cardiac osculation, with blood test positive to an active form of Herpes virus 1 which caused neurological problems and loss of balance. In this case, three intravenous doses were administered three times at an interval of five days, followed by a fourth dose administered at the level of the vertebral column. Already after two months, the horse started to move again, almost completely regaining balance;

A case of a nineteen-year-old horse almost completely retired from competitive activity due to a general physical deterioration, which, after the administration of $200 \times 10^3$ cells, twice at an interval of a week and with repeated treatment, after three months returned to being one of the best in his category (in jumping competitions, jumping heights of 1.35-1.40 m).

The same type of treatment was applied to very old dogs and gave the same results. In dogs the following pathologies were treated:

Two cases of dogs with torsion of the stomach: the first was a six-year-old Great Dane subjected to a surgical operation but with a relapse after one week and therefore again subjected to another operation. After a first administration of $150 \times 10^3$ cells, the dog started eating again and, after two doses at an interval of one week, the dog returned to its normal activity.

The second case was a ten-year-old female Great Dane, suffering from arthrosis, diagnosed with diabetes, and having had a hysterectomy-ovariectomy. Four months after the operation, she had a torsion of the stomach with a subsequent surgical operation which, however, did not bring a great improvement. At this point, two doses were administered, at an interval of one week and four other cycles in the following four months. Today, eight months after the last cycle, the dog not only has a normal glycemia but also her ability to walk has improved by 80%.

Finally, there was a case of a mongrel dog, 13 years old, male, with paresis of the rear limbs and incontinent. Until the treatment by the method of the invention, it had only been treated with cortisone, without appreciable results. Fifteen days after the cortisone was suspended, the cells were taken and the dog was subjected to a cycle of two doses at an interval of a week. Six days after the last treatment, the dog had not only reacquired the use of its legs, but was urinating and defecating normally.

The results obtained by the method according to the invention make this procedure extremely versatile, thanks to the fact that, at the moment, no "in vivo" technique provides for expanding pluripotent cells. Moreover, the lack of any form of rejection or infection following the administration in all the case histories reported above makes this technique suitable for auto-transplant procedures.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for expanding adult stem cells from blood comprising:
    a) obtaining a sample of blood of an adult mammal;
    b) immediately after the sample of blood has been taken from the mammal, treating the sample of blood in vitro with MCSF (macrophage colony stimulating factor) at a concentration of about 8-15 nM MCSF to obtain expanded stem cells in the sample of blood; and
    c) purifying the expanded stem cells.

2. The method according to claim 1, wherein the blood is peripheral blood.

3. The method according to claim 1, wherein the in-vitro treatment with MCSF is performed for about 24 to 96 hours.

4. The method according to claim 3, wherein the in-vitro treatment with MCSF is performed for about 48 to 72 hours.

5. The method according to claim 1, wherein the in-vitro treatment is begun not more than about 10 minutes after the sample of blood has been taken from the mammal.

6. The method according to claim 5, wherein the in-vitro treatment is begun not more than about 5 minutes after the sample of blood has been taken from the mammal.

7. The method according to claim 1, further comprising:
    d) expanding the purified stem cells via an in-vitro treatment with MCSF at a concentration of about 35-55 nM for about 24-72 hours.

8. The method according to claim 7, wherein the concentration of MCSF in step d) is about 50 nM.

9. The method according to claim 7, wherein at least one of step b) and step d) is performed for about 24-48 hours.

10. The method according to claim 1, wherein the concentration of MCSF in step b) is about 10 nM.

11. The method according to claim 1, wherein step c) comprises fractioning on a Ficoll gradient.

12. The method according to claim 1, wherein the mammal is selected from the group consisting of a human, a horse, a cat, and a dog.

* * * * *